US008987207B2

(12) United States Patent
Linguegliа et al.

(10) Patent No.: US 8,987,207 B2
(45) Date of Patent: Mar. 24, 2015

(54) PEPTIDES WHICH HAVE ANALGESIC EFFECTS AND WHICH INHIBIT ASIC CHANNELS

(75) Inventors: Éric Lingueglia, Nice (FR); Sylvie Diochot, Valbonne (FR); Anne Baron-Forster, Valbonne (FR); Miguel Salinas, Cagnes-sur-Mer (FR); Michel Lazdunski, Nice (FR)

(73) Assignee: Centre National de la Recherche Scientifique—CNRS, Paris Cedex (FR)

( * ) Notice: Subject to any disclaimer, the term of this patent is extended or adjusted under 35 U.S.C. 154(b) by 0 days.

(21) Appl. No.: 13/812,457

(22) PCT Filed: Jul. 26, 2011

(86) PCT No.: PCT/FR2011/051800

§ 371 (c)(1), (2), (4) Date: Mar. 29, 2013

(87) PCT Pub. No.: WO2012/022894

PCT Pub. Date: Feb. 23, 2012

(65) Prior Publication Data

US 2013/0196923 A1 Aug. 1, 2013

(30) Foreign Application Priority Data

Jul. 26, 2010 (FR) ..................................... 10 03136

(51) Int. Cl.
*A61K 38/00* (2006.01)
*G01N 33/567* (2006.01)
*C07K 14/46* (2006.01)

(52) U.S. Cl.
CPC *C07K 14/46* (2013.01); *A61K 38/00* (2013.01)
USPC ........................... 514/17.6; 436/501; 530/324

(58) Field of Classification Search
None
See application file for complete search history.

(56) References Cited

U.S. PATENT DOCUMENTS 5,877,026 A 3/1999 Lampe

OTHER PUBLICATIONS

Gutstein et al., "Opioid Analgesics", Chapter 21, pp. 547-590, 2006.
Yennurjalingam et al., "Recent Developments in Cancer Pain Assessment and Management", *Supportive Cancer Therapy*, vol. 1, Nov. 2, pp. 97-110, Jan. 2004.
Mizoguchi et al., "New Therapy for Neuropathic Pain", Department of Physiology and Anatomy, Tohoku Pharmaceutical University, *International Review of Neurobiology*, vol. 85, pp. 249-260, 2009.
Waldmann et al., "Molecular Cloning of a Non-Inactivating Proton-Gated Na $^+$Channel Specific for Sensory Neurons", *The Journal of Biological Chemistry*, vol. 272, No. 34, pp. 418-424, Aug. 1997.
Lingueglia et al., "Acid-Sensing Ion Channels in Sensory Perception", *The Journal of Biological Chemistry*, vol. 282, No. 24, pp. 17325-17329, Jun. 2007.
Jasti et al., "Structure of Acid-sensing Ion Channel 1 at 1.9 Å Resolution and Low pH", *Nature*, vol. 449, pp. 316-323, Sep. 2007.
Lingueglia et al., "A Modulatory Subunit of Acid Sensing Ion Channels in Brain and Dorsal Root Ganglion Cells", *The Journal of Biological Chemistry*, vol. 272, No. 47, pp. 29778-29783, Nov. 1997.
Benson et al., "Heteromultimers of DEG/ENaC Subunits Form $H^+$-gated Channels in Mouse Sensory Neurons", *Proc. Natl. Acad. Sci. (PNAS)*, vol. 99, No. 4, pp. 2238-2243, Feb. 2002.
Waldmann et al., "A Proton-gated Cation Channel Involved in Acid-Sensing"*Nature*, vol. 386, pp. 173-177, Mar. 1997.
Noël et al., "Current Perspectives on Acid—Sensing ION Channels: New Advances and Therapeutic Implications", *Expert Rev. Clin. Pharmacol.* pp. 331-346, 2010.
Bassler et al., "Molecular and Functional Characterization of Acid-Sensing Ion Channel (ASIC) 1b", *The Journal of Biological Chemistry*, vol. 276, No. 36, pp. 33782-33787, Sep. 2001.
Chen et al., "A Sensory Neuron-specific, Proton-gated ION Channel", *Proc. Natl. Acad. Sci.* U.S.A., vol. 95, pp. 10240-10245, Aug. 1998.
Steen et al., "Pain due to Experimental Acidosis in Human Skin: Evidence for Non-adapting Nociceptor Excitation" *El Sevier*, Neuroscience Letters 199 : 29-32, Sep. 1995.
Issberner et al., "Pain due to Tissue Acidosis: a Mechanism for Inflammatory and Ischemic Myalgia?" *El Sevier*, Neuroscience Letters 208, pp. 191-194, Mar. 1996.
Ugawa et al., "Amiloride-Blockable Acid-Sensing Ion Channels are Leading Acid Sensors Expressed in Human Nociceptors", *The Journal of Clinical Investigation*, vol. 110, No. 8, pp. 1185-1191, Oct. 2002.
Escoubas et al., "Isolation of a Tarantula Toxin Specific for a Class of Proton-gated Na $^+$Channels", *The Journal of Biological Chemistry* Biol. Chem., 275(33) : 25116-25121, May 2000.
Diochot et al., "A New Sea Anemone Peptide, APETx2, Inhibits ASIC3, a Major Acid-Sensitive Channel in Sensory Neurons", *EMBO Journal*, vol. 23, No. 7, pp. 1516-1525, Mar. 2004.
Abbott, et al., "Morphine Analgesia and Tolerance in the Tail-Flick and Formalin Tests: Dose-Response Relationships", Department of Pharmacology, Pharmacology Biochemistry & Behavior, vol. 17, pp. 1213-1219, May 1982.
Cridland et al., "Bombesin, Neuromedin C and Neuromedin B Given Intrathecally Facilitate the Tail Flick Reflex in the Rat", Department of Physiology and Psychiatry, McGill University, Brain Res., 584(1-2) : 163-168, Feb. 1992.
Kim et al., "Effects of Sympathectomy on a Rat Model of Peripheral Neuropathy", Marine Biomedical Institute and Departments of Anatomy and Neurosciences and Physiology and Biophysics, Univ. of Texas Medical Branch, *Pain*, 55 : 85-92, Mar. 1993.

(Continued)

*Primary Examiner* — John Ulm
(74) *Attorney, Agent, or Firm* — Patterson Thuente Pedersen, P.A.

(57) ABSTRACT

Novel isolated peptides which induce analgesia and which inhibit ASIC channels (Acid Sensing Ion Channels), to the polynucleotides encoding these peptides, and also to the pharmaceutical compositions, host cells, and vectors comprising these peptides and the polynucleotides encoding these peptides. In particular, these peptides are isolated from the venom of the snake *Dendroaspis polylepis*. The present invention also relates to the use of these peptides as a diagnostic tool or as a medicament, particularly as an analgesic, or for identifying analgesic molecules or molecules which inhibit ASIC channels.

20 Claims, 7 Drawing Sheets

(56) References Cited

OTHER PUBLICATIONS

Reeh and Steen, "Chapter 8 Tissue acidosis in nociception and pain", Progress in Brain Research, vol. 113 : 143-151, 1996.

Ankier, Stephen I., "New Hot Plate Tests to Quantify Antinociceptive and Narcotic Antagonist Activities", *European Journal of Pharmacology* 27(1974) 1-4, Mar. 1974.

Bannister et al., "Opioid Hyperalgesia", Currently Opinion in Supportive and Pallative Care, 4, pp. 1-5 (2010).

Calvino et al., "Douleur, Inflammation et Interactions Systéme Nerveaux/Systéme Immunitaire", Instiut UPSA de la Douleur, 137 pages (French) (2007).

Deval et al., "ASIC3, A Sensor of Acidic and Primary Inflammatory Pain", The EMBO Journal, 27, pp. 3047-3055 (2008).

Deval et al., "Acid-sensing Ion Channels in Postoperative Pain", The Journal of Neuroscience, 31(16), pp. 6059-6066 (2011).

Dubéet al., "Electrophysiological and in vivo Characterization of A-317567, a Novel Blocker of Acid Sensing Ion Channels", Pain., 117(1-2), pp. 88-96 (2005).

He et al., "Cloning and Purification of α-neurotoxins from King Cobra (Ophiophagus Hannah)," Toxicon, 44, pp. 295-303 (2004).

Hesselager et al., "pH Dependency and sensitization Kinetics of Heterologously Expressed Combinations of Acid-sending Ion Channel Subunits", The Journal of Biological Chemistry, vol. 279, No. 12, pp. 11006-11015 (2004).

Hylden et al., "Intrathecal Morphine in Mice: A New Technique", European Journal of Pharmacology, 67, pp. 313-316 (1980).

Jones et al., "Acid-Induced Pain and Its Modulation in Humans", The Journal of Neuroscience, 24(48), pp. 10974-10979 (2004).

Voilley et al., "Nonsteroid Anti-Inflammatory Drugs Inhibit Both the Activity and the Inflammation-Induced Expression of Acid-Sensing Ion Channels in Nociceptors", The Journal of Neurosicence, 21(20), pp. 8026-8033 (2001).

Waldmann et al., "$H^+$-gated Cation Channels: Neuronal Acid Sensors in the NaC/DEG Family of Ion Channels", Current Opinion in Neurobiology, vol. 8, Issue 3, pp. 418-424 (1998).

Wemmie et al., "Acid-sensing Ion Channels: Advances, Questions and Therapeutic Opportunities", Trends in Neuroscience, (10), pp. 578-586 (2006).

Woolfe et al., "The Evaluation of the Analgesic Action of Pethidine Hydrochloride (Demerol)" Department of Pharmacology, Manchester University, pp. 300-307 (Nov. 1943).

Mazzuca et al., "A tarantula peptide against pain via ASIC1a channels and opioid mechanisms", Nature Neuroscience, vol. 10, No. 8, Aug. 2007, pp. 943-945 and Supplementary Text and Figures.

A

ASICalgin-1 LKCYQHGKVVTCHRDMKFCYHNTGMPFRNLKLILQGCSSSCSETENNKCCSTDRCNK
ASICalgin-2 LKCFQHGKVVTCHRDMKFCYHNTGMPFRNLKLILQGCSSSCSETENNKCCSTDRCNK

B

*M K T L L L T L L V V T I V C L D L* 18
ATG AAA ACT CTG CTG CTG ACC TTG CTG GTG GTG ACA ATC GTG TGC CTA GAC TTA 54
*G Y S* L K C Y Q H G K V V T C H R D 36
GGA TAC TCC CTG AAA TGT TAC CAA CAT GGT AAA GTT GTG ACT TGT CAT CGA GAT 108
M K F C Y H N T G M P F R N L K L I 54
ATG AAG TTT TGC TAT CAT AAC ACT GGC ATG CCT TTT CGA AAT CTC AAG CTC ATC 162
L Q G C S S S C S E T E N N K C C S 72
CTA CAG GGA TGT TCT TCT TCG TGC AGT GAA ACA GAA AAC AAT AAG TGT TGC TCA 216
T D R C N K * 78
ACA GAC AGA TGC AAC AAA TAG ctctacgagtggctaaattcattgagttttgctctcatccattgtggaccatccttg 294
aaaatttatgcttgtggcctttacccaccagatggtccatcatcccctctcccctgctttcttgatacctcatcatctttcccttttctcttgttc 391
tgtaatttccttctgctagttctgtagtttgagaatcaaataaaactcagcattc-Poly(a+) 446

Figure 1

PEPTIDES WHICH HAVE ANALGESIC EFFECTS AND WHICH INHIBIT ASIC CHANNELS

PRIORITY CLAIM

This application is a National Phase entry of PCT Application No. PCT/FR2011/051800, filed Jul. 26, 2011, which claims priority from French Application No. 1003136, filed Jul. 26, 2010, the disclosures of which are hereby incorporated by referenced herein in their entirety.

A Sequence Listing appended to the present specification is herein incorporated by reference in its entirety.

FIELD OF THE INVENTION

The present invention relates to novel peptides which induce analgesia and which inhibit ASIC channels (Acid Sensing Ion Channels), more particularly homomeric ASIC1a channels, homomeric ASIC1b channels and/or heteromeric channels containing at least one subunit chosen from ASIC1a and ASIC1b, to the polynucleotides encoding said peptides, and also to the pharmaceutical compositions, host cells and vectors contained therein. In particular, said peptides exhibit a minimum of 56% identity with the amino acid sequence SEQ ID NO: 1 in the appended sequence listing. They are in particular the two 57-amino acid peptides ASICalgin-1 (π-Dp1) and ASICalgin-2 (π-Dp2) isolated from the venom of the snake *Dendroaspis polylepis* (black mamba), of sequences SEQ ID NO: 2 and SEQ ID NO: 3, respectively.

The present invention also relates to the use thereof for obtaining a diagnostic tool or a medicament, in particular an analgesic, and also for identifying analgesic molecules or molecules which inhibit ASIC channels.

The present invention has in particular an application in the prevention or treatment of pain, in particular pain associated with the activation of ASIC channels (for example inflammatory, neuropathic, cancer-related, post-operative, musculoskeletal, visceral, etc., pain), of central neurological diseases (for example, post-traumatic stress, depression, anxiety, strokes, epilepsy, multiple sclerosis, cerebral inflammations, neurodegenerative diseases, etc.), and of pathological conditions in which the involvement of ASIC channels has been proposed (for example, inflammations, cancers, fibromyalgia, irritable bowel syndrome, etc.).

In the description below, the reference number between square brackets ([ ]) refer to the list of references presented at the end of the text.

BACKGROUND OF THE INVENTION

The taking into account and treatment of pain are essential aspects of improving the quality of life of patients. Pain affects a considerable number of individuals, about 60 million in Europe each year, which represents an annual cost of 1 billion dollars in analgesic medicaments for treating said pain. The amounts spent annually throughout the world on analgesic medicaments can be evaluated at approximately 25 billion dollars, and should reach 42 billion in 2010. Pain is divided up into two categories: acute pain and chronic pain. Acute pain corresponds to rapid and brief pain which is limited over time. Conversely, chronic pain is a persistent pain which can be linked, for example, to hyperalgesia, and which constitutes an enormous disease burden, affecting approximately 20% of adults and 50% of the elderly population.

The treatment of pain is based essentially on the prescription of anti-inflammatories, whether they are nonsteroidal (NSAIDs) or steroidal (corticoids), and of weak or strong opiates. NSAIDs form the therapeutic class most widely prescribed throughout the world, owing to their great efficacy both on inflammation and on pain itself. They are used in all types of inflammatory pain, whether acute or chronic [Bertin and Vergne-Salle, 2007] [1]. When NSAIDs and/or corticoids are not sufficient to relieve inflammatory pain, the prescribing physician combines a non-anti-inflammatory analgesic, for example paracetamol, weak opioids (codeine, tramadol), and, if the pain continues to be resistant to the treatment, strong opioids (morphine, oxycodone, fentanyl) [Gutstein & Akil, 2006] [2].

While NSAIDs are very effective, they nevertheless remain great purveyors of adverse side effects. Among the most standard adverse side effects, digestive effects are very frequent and limit the use of NSAIDs in many clinical situations. There are also renal, cutaneous, mucosal, allergic and respiratory, hematological, hepatic and, finally, neurosensory and psychological adverse side effects [Bertin and Vergne-Salle, 2007, mentioned above] [1]. In addition, NSAIDs are not effective in all types of pain. Opioids also play a major role in combating pain, but can cause hallucinatory phenomena and cardiorespiratory depression. Analgesics can also be a source of dependence, for instance morphine, methadone, etc., dependence. There are also cases of habituation to analgesics, that is to say the dose necessary to obtain a constant effect must be increased. This habituation increases over time and therefore leads to the need to increase the doses and can lead to ineffectiveness of the medicament. Indeed, the dose necessary to relieve pain can become greater than the toxic dose of said medicament. Finally, treatment with opioids can also be associated with adverse effects such as severe constipation or hyperalgesia when the treatment is stopped (post-operative pain, for example) [Gutstein & Akil, 2006, mentioned above; Bannister & Dickenson, 2010] [2, 3].

Despite the diversity of the existing therapeutic arsenal, many types of pain remain relatively insensitive to the known analgesics, such as neuropathic pain following damage to the nervous system (50% of patients experience no relief), chronic visceral pain such as irritable bowel syndrome or chronic inflammatory bowel disease, fibromyalgia, pain associated with cancers and bone metastases, etc. [Yennurajalingam et al., 2004; Mizoguchi et al., 2009] [4, 5].

In this context, the discovery of novel analgesics compensating for these deficiencies and drawbacks and/or novel analgesic targets should therefore represent real progress.

Research in the pharmaceutical industry on pain has over the past few years resulted only in a few limited developments. Mention may, for example, be made of triptans for migraine and certain novel medicaments of which the use still remains limited, such as the combination of tetrahydrocannabinol and cannabidiol for cancer-related and neuropathic pain. In fact, the progress made over the last two decades comes essentially from a better use and adjustments of the dosage of the available analgesics. None of the major families of these analgesics has a benefit/risk ratio which is optimal, because of a limited efficacy and/or considerable side effects.

Among the molecular targets identified over the past few years, ion channels hold a particularly important place because they are directly involved in the detection and transmission of pain signals by sensory and central neurons. ASIC channels (Acid Sensing Ion Channels) are cationic channels activated by acidification of the extracellular medium (extracellular acidosis) [Waldmann & Lazdunski, 1998; Wemmie et al., 2006; Lingueglia et al., 2007] [6, 7, 8]. Thus far, four genes encoding at least seven subunits (ASIC1a, ASIC1b, ASIC1b2, ASIC2a, ASIC2b, ASIC3 and ASIC4) have been identified in mammals. Functional ASIC channels result from the association of various ASIC subunits as trimers [Jasti et al. 2007] [9] resulting in homomeric or heteromeric channels [Lingueglia et al., 1997; Benson et al., 2002; Hesselager et al., 2004] [10, 11, 12]. ASIC channels are essentially expressed in nociceptive sensory neurons of the peripheral nervous system and in central nervous system neurons [Waldmann et al., 1997a; Lingueglia et al, 2007, mentioned above; Noel et al., 2010] [13, 8, 14]. Although the ASIC1a and ASIC2 isoforms are present in both the central nervous system and the peripheral nervous system, the expression of the ASIC1b and ASIC3 isoforms is restricted to sensory neurons [Waldmann et al., 1997b; Bassler et al., 2001; Chen et al., 1998] [15, 16, 17].

It has been postulated that the ASIC channels expressed by sensory neurons, and in particular the ASIC3 channel, are capable of detecting extracellular acidifications that may develop during ischemia, inflammation, a hematoma, a fracture, a lesion, a surgical procedure (post-operative pain), or the development of certain tumors [Reeh and Steen, 1996] [18]. As it happens, it has been known for several years now that extracellular acidosis causes pain [Steen et al., 1995a; Issberner et al., 1996] [19, 20], and experiments carried out on healthy human volunteers [Ugawa et al., 2002; Jones et al., 2004] [21, 22] have shown the involvement of ASIC channels in acidic skin pain by means of amiloride and certain NSAIDs, which are nonspecific inhibitors of ASIC channels [Waldmann et al., 1997a, mentioned above; Voilley et al., 2001] [13, 23]. The important role of certain ASIC channels expressed in central nervous system neurons in neuronal activity (synaptic plasticity of the hippocampus, of the amygdala) and the neuromodulation of the transmission of pain information (ASIC 1a channels) by spinal cord neurons has also been demonstrated [Noel et al., 2010] [14].

Until recently, the repertoire of active ligands capable of inhibiting ASIC channels was mainly limited to amiloride, to certain NSAIDs and to the compound A-317567 [Dubé et al., 2005] [24]. However, none of these molecules is absolutely specific for ASIC channels or for a particular ASIC subunit. With the aim of identifying effectors specific for ASIC channels, a very large number of scorpion, bee, spider, snake or sea anemone venoms have been screened. Recently, two animal peptide toxins, PcTx1 and APETx2, have been identified which inhibit homomeric ASIC1a channels and the channels containing the ASIC3 subunit, respectively [Escoubas et al., 2000; Diochot et al., 2004] [25, 26]. The peripheral (subcutaneous) injection of APETx2 induces an analgesic effect on inflammatory and acidic pain in rats [Deval et al., 2008] [27] and on post-operative pain in rats after intra-operative application of APETx2 [Deval et al., J. Neurosci., 31(16): 6059-6066, 2011] [36], while the central injection of PcTx1 induces a powerful analgesic effect in mice [Mazzuca et al., 2007] [28]. The analgesic effects of these two toxins have made it possible to demonstrate the involvement in ASIC channels in the perception and transmission of pain information.

There is therefore a real need to identify other effectors specific for ASIC channels or for a particular ASIC subunit, capable of exhibiting an analgesic effect while at the same time compensating for the deficiencies, drawbacks and obstacles of the prior art analgesics.

DESCRIPTION OF THE INVENTION

The inventors have now discovered and identified, from the venom of the snake *Dendroaspis polylepis* (black mamba), novel peptides which induce analgesia and which inhibit ASIC channels (Acid Sensing Ion Channels), more specifically homomeric ASIC1a channels, homomeric ASIC1b channels, heteromeric ASIC1a+2a channels and heteromeric ASIC1a+1b channels.

They are in particular the peptides ASICalgin-1 (π-Dp1) and ASICalgin-2 (π-Dp2) which, after central (intrathecal and intracerebroventricular) injection in vivo in mice, exhibit a powerful analgesic effect on different pain modes (chemical, thermal, inflammatory), which is comparable to that of morphine but largely independent of opiate receptor activation. In addition, these peptides do not exhibit neurotoxic effects when they are injected centrally. When administered by subcutaneous peripheral injection, these peptides also exert an analgesic effect with reversion of inflammatory hyperalgesia. These two peptides are the first peptides extracted from the venom of *Dendroaspis polylepis* (black mamba) to exhibit an analgesic effect.

Without being limited by this explanation, the most probable mechanism of action of these peptides appears to result from the inhibition of ASIC ion channels which play an important role in the perception, transmission and modulation of pain information. Indeed, these peptides efficaciously inhibit homomeric ASIC1a channels, homomeric ASIC1b channels and/or heteromeric channels containing an ASIC1a and/or ASIC1b subunit of rats and humans. These two peptides are in particular the first known inhibitors of homomeric ASIC1b and ASIC1a channels and heteromeric ASIC1a+ASIC1b and ASIC1a+ASIC2a channels.

The ASICalgin-1 (π-Dp1) and ASICalgin-2 (π-Dp2) peptides also inhibit the native ASIC currents present in sensory neurons and in central neurons. They have no effect on the TRPV1 current activated by capsaicin and by heat and which is itself also involved in pain perception. They do not modify the electrical properties of neurons in the basal state, but reduce neuronal excitability in response to an extracellular acidification capable of activating ASIC channels.

The ASICalgin-1 (π-Dp1) and ASICalgin-2 (π-Dp2) peptides therefore have, in rodents, powerful analgesic properties comparable to those of morphine, which continue to be observed when the opiate receptors are blocked, and which can be explained by their capacity to specifically inhibit certain rodent and human ASIC channels. The central injection of said peptides induces no toxicity (neurotoxicity, convulsions, etc.), nor any effect on motor activity (accelerating rotarod test).

The ASICalgin-1 (π-Dp1) and ASICalgin-2 (π-Dp2) peptides can therefore be envisioned as novel molecules having a therapeutic potential against pain (for example, cancer-related pain, neuropathic pain, post-operative pain, etc.) in humans.

A subject of the present invention is therefore a peptide comprising:

(i) the amino acid sequence (SEQ ID NO: 1)
LKCX[4]QHGKVVTCHRDMKFCYHNTGMPFRNLKLILQGCSSSCSETENNKC
CSTDRCNK wherein X4 represents any amino acid;

or (ii) a natural or synthetic sequence exhibiting an identity of at least 56% with the sequence SEQ ID NO: 1, preferably of at least 70%, preferentially of at least 80%, most preferentially of at least 98%, and retaining the biological properties of the peptides comprising the sequence SEQ ID NO: 1 as described above, namely which induce analgesia and which inhibit at least one ASIC channel containing at least one subunit chosen from the group consisting of the ASIC1a and ASIC 1b subunits.

Said peptides according to the invention operate more particularly as a blocker of homomeric ASIC1a channels, homomeric ASIC1b channels and/or heteromeric ASIC channels containing at least one subunit chosen from the group consisting of the ASIC1a and ASIC1b subunits, in particular heteromeric ASIC1a+ASIC1b channels and/or heteromeric ASIC1a+ASIC2a channels.

For the purpose of the present invention, the term "blocker" is intended to mean a peptide capable of inhibiting in a concentration-dependent manner the current produced by the abovementioned channels. For example, it is a peptide which, like PcTx1 [Escoubas et al., 2000, mentioned above] [25], is capable of inhibiting, at a concentration of 1 nM, 50% of the current produced by the homomeric ASIC1a channels, or which, like APETx2 [Diochot et al., 2004, mentioned above] [26], is capable of inhibiting, at a concentration of 2 μM, 50% of the current produced by the rat heteromeric ASIC1a+ASIC3 channels.

Preferably, said peptides according to the invention are extracted from the venom of the snake *Dendroaspis polylepis*. For example, they are isolated from the venom by sequential fractionation by means of a reverse-phase-polarity high performance liquid chromatograph (RP-HPLC). Said peptides can also be prepared by DNA recombination methods or by chemical synthesis.

Preferably, said peptides according to the invention comprise the ASICalgin-1 (π-Dp1) or ASICalgin-2 (π-Dp2) peptide having the sequence SEQ ID NO: 1 wherein X4 represents Y or F, respectively (SEQ ID NO: 2 and 3, respectively).

A subject of the present invention is also a polynucleotide comprising a nucleotide sequence encoding a peptide according to the invention.

Preferably, said polynucleotide according to the invention comprises a nucleotide sequence:

```
                                        (SEQ ID NO: 4)
atgaaaactctgctgctgaccttgctggtggtgacaatcgtgtgcctaga

cttaggatactccctgaaatgt⁷³txx⁷⁵caacatggtaaagttgtgact

tgtcatcgagatatgaagttttgctatcataacactggcatgccttttcg

aaatctcaagctcatcctacagggatgttcttcttcgtgcagtgaaacag

aaaacaataagtgttgctcaacagacagatgcaacaaatag;
Or

                                        (SEQ ID NO: 22)
ctgaaatgt¹⁰txx¹²caacatggtaaagttgtgacttgtcatcgagata

tgaagttttgctatcataacactggcatgccttttcgaaatctcaagctc

atcctacagggatgttcttcttcgtgcagtgaaacagaaaacaataagtg

ttgctcaacagacagatgcaacaaatag;
```

wherein $^{73}$txx$^{75}$ and $^{10}$txx$^{12}$ represent tac, tat, ttt or ttc.

Preferably, said polynucleotide according to the invention comprises a nucleotide sequence such that it can hybridize under stringent conditions with the nucleotide sequence SEQ ID NO: 4 or SEQ ID NO: 22, or a sequence complementary thereto. For example, it is a polynucleotide which comprises a natural or synthetic sequence exhibiting an identity of at least 76% with the sequence SEQ ID NO: 4 or the sequence SEQ ID NO: 22, preferably of at least 80%, most preferentially of at least 98%.

A subject of the present invention is also a vector comprising a polynucleotide according to the invention.

Preferably, said vector according to the invention is an expression vector.

A subject of the present invention is also a host cell comprising one or more peptides according to the invention, polynucleotides according to the invention or vectors according to the invention.

A subject of the present invention is also a pharmaceutical composition comprising one or more peptides according to the invention, polynucleotides according to the invention, vectors according to the invention or host cells according to the invention. A pharmaceutical composition according to the invention may also comprise one or more pharmaceutically acceptable vehicles (calcium carbonate, starch, talc, lactose, magnesium stearate, acacia gum, etc.) and be in the form of a solution, suspension, paste, gel capsule, tablet, capsule, powder, granule, lyophilisate, controlled-release system, microparticle, micro- or nanosphere, liposome, etc. A pharmaceutical composition according to the invention can be administered orally, intramuscularly, intravenously, subcutaneously, topically, via the pulmonary route, intranasally, buccally, rectally, sublingually, intradermally, intraperitoneally, intrathecally, etc. The effective amount of active ingredient (peptide, polynucleotide, vector or host cell according to the invention), in a pharmaceutical composition according to the invention, can vary such that an effective dose is obtained and that an analgesic amount is administered to a mammal. The dosage administered to a particular mammal depends on several factors: the route of administration, the duration of treatment, the size and physical condition of the mammal, the potency of the active ingredient and the response of the mammal to said active ingredient. For example, an effective analgesic amount of active ingredient administered intrathecally generally ranges from approximately 5 ng/kg to 500 μg/kg of bodyweight of the mammal, preferably from approximately 50 ng/kg to 50 μg/kg of bodyweight of the mammal, most preferentially from approximately 500 ng/kg to 5 μg/kg of bodyweight of the mammal. The effective amounts of active ingredient can vary when other routes of administration are used. An effective analgesic amount can be estimated by testing the active ingredient in one or more pain tests mentioned hereinafter at a dose which can vary according to one or more criteria cited above, in order to determine the effective amount of active ingredient to be administered to a mammal.

A subject of the present invention is also a substance chosen from a peptide according to the invention, a polynucleotide according to the invention, a vector according to the invention, a host cell according to the invention or a pharmaceutical composition according to the invention, for application thereof as a medicament.

Preferably, said medicament is an analgesic, for example intended for the prevention or treatment of pain involving the activation of ASIC channels, in particular ASIC channels containing at least one subunit chosen from the group consisting of the ASIC1a and ASIC1b subunits, most particularly of the homomeric ASIC1a channels, homomeric ASIC1b channels, heteromeric ASIC1a+ASIC1b channels and/or heteromeric ASIC 1a+ASIC2a channels. For example, the pain may (i) result from the activation of central or peripheral ASIC channels or (ii) induce activation thereof. For example, the pain is pain, in particular pain associated with ASIC channel activation, chosen from the group comprising inflammatory, neuropathic, cancer-related, post-operative, musculoskeletal, visceral, etc., pain.

Preferably, said medicament is intended for the prevention or treatment of a pathological condition involving the activation of ASIC channels, in particular of ASIC channels containing at least one subunit chosen from the group consisting of the ASIC1a and ASIC1b subunits, most particularly the homomeric ASIC1a channels, homomeric ASIC1b channels, heteromeric ASIC1a+ASIC1b channels and/or heteromeric ASIC 1a+ASIC2a channels. For example, it involves pathological conditions chosen from the group comprising inflammations, cancers, fibromyalgia, irritable bowel syndrome, etc.

Preferably, said medicament is intended for the prevention or treatment of a central neurological disease, for example chosen from the group comprising post-traumatic stress, depression, anxiety, strokes, epilepsy, central inflammations, multiple sclerosis, neurodegenerative diseases, etc.

Preferably, said medicament is administered parenterally, namely locoregionally or centrally (intraperitoneally, peridurally, intrathecally, intracerebroventricularly, intradermally, etc.) and systemically (intramuscularly, intravenously, subcutaneously, etc.), orally, locally (transcutaneously, etc.) or via the respiratory route (inhalation, instillation, etc.). Most preferentially, said medicament is administered intrathecally, peridurally, intracerebroventricularly, intraperitoneally or subcutaneously.

A subject of the present invention is also a substance chosen from a peptide according to the invention, a polynucleotide according to the invention, a vector according to the invention, a host cell according to the invention or a pharmaceutical composition according to the invention, for use thereof as a diagnostic tool.

A subject of the present invention is also a method for identifying a compound which mimics the analgesic activity of a peptide according to the invention, comprising the following steps:

a) determining the analgesic activity of a peptide according to the invention;
b) determining the analgesic activity of a candidate compound;
c) comparing the analgesic activities obtained in steps a) and b);
d) selecting the candidate compound which has an analgesic activity equivalent to or greater than that of a peptide according to the invention.

A subject of the present invention is also a method for identifying a compound which mimics the analgesic activity of a peptide according to the invention, comprising the following steps:

a) bringing a peptide according to the invention into contact with a sample, and measuring the binding of said peptide with said sample;
b) adding a candidate compound, and evaluating the effect of said compound on the binding of said peptide with said sample;
c) selecting the candidate compound capable of modulating the binder of said peptide with said sample.

For the purpose of the present invention, the expression "compound which mimics the analgesic activity of a peptide according to the invention" is intended to mean a candidate compound capable of inducing analgesia and of binding the ASIC channels to which the peptides according to the invention bind or else of acting in a physiological manner identical or similar to that of the peptides according to the invention, namely modulating (inhibiting or stimulating), reversibly and in a concentration-dependent manner, the current produced by at least one channel containing at least one subunit chosen from the group consisting of the ASIC1a and ASIC1b subunits, in particular by homomeric ASIC1a channels, homomeric ASIC1b channels, heteromeric ASIC1a+ASIC1b channels and/or heteromeric ASIC1a+ASIC2 channels. For example, it involves a peptide which, like PcTx1 [Escoubas et al., 2000, mentioned above] [25], is capable of inhibiting, at a concentration of 1 nM, 50% of the current produced by the homomeric ASIC1a channels, or which, like APETx2 [Diochot et al., 2004, mentioned above] [26], is capable of inhibiting, at a concentration of 2 nM, 50% of the current produced by rat heteromeric ASIC1a+ASIC3 channels.

For the purpose of the present invention, the term "sample" is intended to mean cells or tissue isolated beforehand from the whole organism or from immortalized cell lines, of insects or mammals.

The term "analgesic activity" refers to the capacity of a peptide according to the invention to treat pain in a mammal, or to reduce pain, as demonstrated by one or more conventional laboratory models for testing pain or evaluating analgesia, such as those described hereinafter. Thus, the analgesic activity of a peptide according to the invention can be determined, for example, by means of one or more of the following in vivo tests: i) tail/paw withdrawal latency (measurement of thermal nociception) [Abott et al., 1982; Cridland and Henry, 1992] [29, 30], ii) hot/cold plate threshold (measurement of thermal nociception) [Woolfe and Macdonald, 1944, Ankier, 1974] [31, 32], iii) von Frey filament threshold or Randall-Selitto test or instrumented pincher test (mechanical nociceptive activity measurement) [Kim et al., 1993] [33], iv) dynamic weight distribution test (measurement of nociceptive activity linked to posture), v) measurement of spontaneous nociceptive behavior, and/or of one or more in vitro tests: for example, screening of candidate compounds by competition in which a peptide according to the invention which has been labeled (for example, with a radiolabel such as $C^{14}$, $H^3$ or $I^{125}$, an enzyme such as peroxidase or alkaline or acid phosphatase, a fluorescent label such as FITC or rhodamine, an antibody, an antigen, biotin, a paramagnetic ion, a latex particle, etc.) is brought into contact with a sample under conditions which allow it to bind to said sample, and the binding of said labeled peptide bound to the sample is measured, and in which the compounds which mimic the activity of said labeled peptide compete with said peptide for binding to the sites on the receptor (ASIC channels containing at least one subunit chosen from the group consisting of the ASIC1a and ASIC1b subunits). Thus, a lower amount of detectable labeling is measured when the test compounds mimic the activity of said peptide by binding to the receptor than when the test compounds do not mimic the activity of said peptide and do not bind the receptor, or bind with less affinity. As an alternative, the competition screening can be carried out with labeling of the candidate compound instead of labeling of the peptide according to the invention. Thus, a higher amount of detectable labeling will be measured when the test compounds mimic the activity of said peptide by binding to the receptor than when the test compounds do not mimic the activity of said peptide and do not bind the receptor, or bind with less affinity.

Examples of methods for identifying compounds which mimic the analgesic activity of peptides are described (without being limited by this description), for example in U.S. Pat. No. 5,877,026 [34].

Other advantages may become further apparent to those skilled in the art on reading the examples below, illustrated by the appended figures, which are given by way of illustration.

BRIEF DESCRIPTION OF THE FIGURES

FIG. 1 represents (A) the amino acid sequence of the ASICalgin-1 (π-Dp1) and ASICalgin-2 (π-Dp2) peptides isolated from the venom of the snake *Dendroaspis polylepis* (SEQ ID No: 2 and 3, respectively), (B) the nucleotide sequence of the complementary DNA (cDNA) encoding ASICalgin-1 (SEQ ID NO: 5). The signal sequence (in italics) and the final peptide (in bold) (cf. SEQ ID NO: 6), and the stop codon (*) are indicated. The sequence of the 5' noncoding end is not represented (corresponding to SEQ ID NO: 9).

EXAMPLES

Example 1

Figure 2:
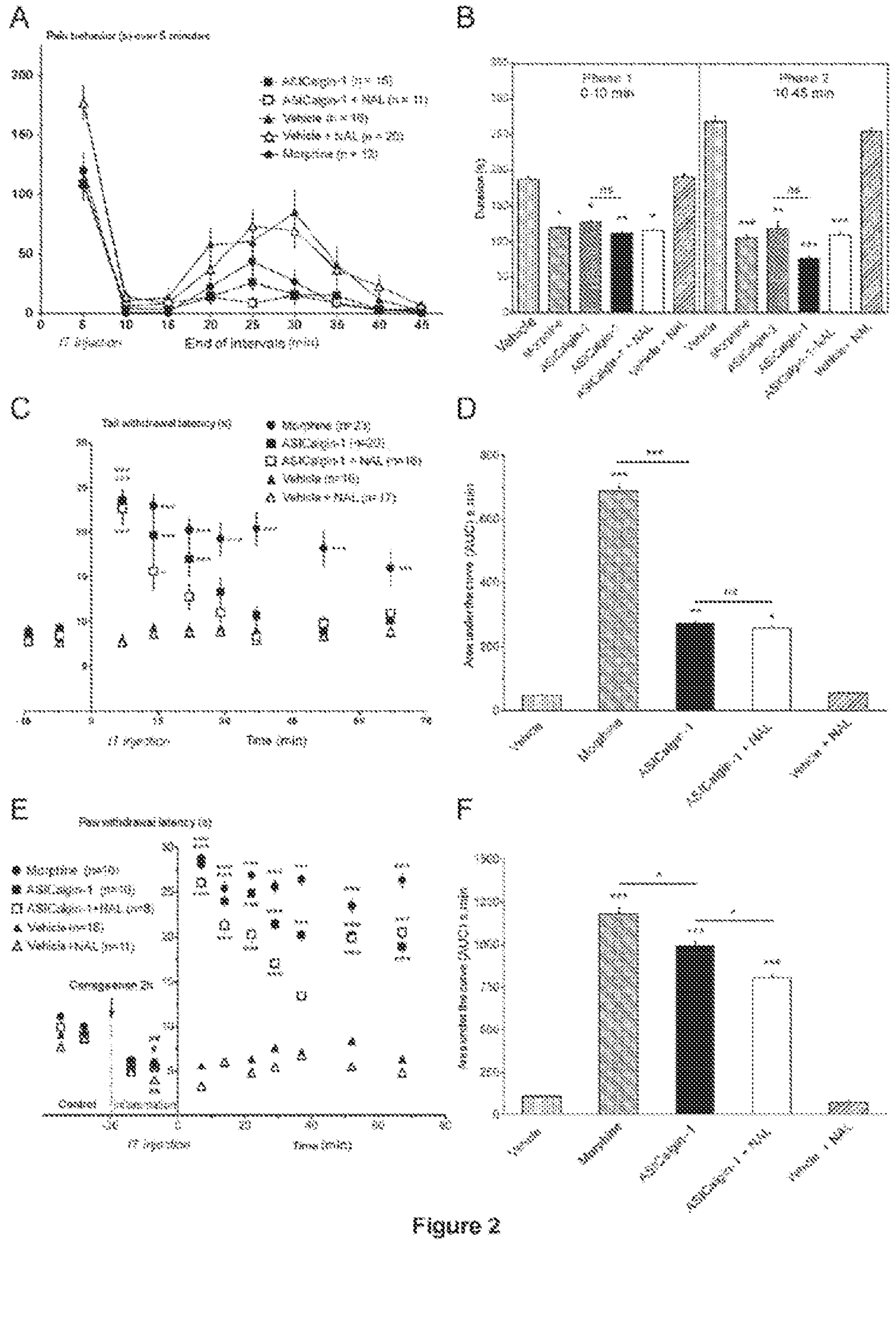
FIG. 2 represents the analgesic effect of the ASICalgin-1 (π-Dp1) and ASICalgin-2 (π-Dp2) peptides in vivo after intrathecal injection in mice. Chemical pain (formol): (A) kinetics of spontaneous pain behavior measured in intervals of 5 minutes, (B) total duration of phase I (0-10 minutes) of acute pain and of phase II (10-45 minutes) of inflammatory pain. Acute thermal pain: (C) kinetics of tail withdrawal latency, (D) mean of the areas under the curve (AUC) measured for each animal. Inflammatory hyperalgesia: (E) kinetics of paw withdrawal latency. Significance of hyperalgesia relative to the control value: #, $p<0.05$; ##, $p<0.01$; ###, $p<0.001$; by ANOVA test followed by a Newman Keuls multiple comparison. (F) mean of the areas under the curve (AUC) measured for each animal, from the hyperalgesic level (T−7 min) The mean values±sem (standard error of the mean) are represented and the number (n) of animals tested is mentioned in the legends. Significance relative to the injection of the vehicle±naxolone (NAL) or else according to where indicated on the figure by a line: not significant ns, $p>0.05$; *, $p<0.05$; , $p<0.01$; *, $p<0.001$; by ANOVA test followed by a Newman Keuls multiple comparison.

Isolation of Two Peptides, ASICalgin-1 (π-Dp1) and ASICalgin-2 (π-Dp2), from the Venom of the Snake *Dendroaspis Polylepis*

Venom and Purification of the Peptide Toxins

The lyophilized venom comes from the company Latoxan (Valence, France). The venom was diluted in acetic acid (1%) and fractionated by passing it over a column containing a Sephadex G50 resin. The peptide fraction was recovered and subsequently fractionated on a High Performance Liquid Chromatography (HPLC) system: 1) The peptide fraction was loaded onto and eluted from a cation exchange column with a pH gradient with the solvents 1% acetic acid, pH 3.0, and 1M ammonium acetate, pH 6.8. The fraction containing the ASICalgins was eluted starting from 60% ammonium acetate. 2) This peptide fraction was loaded onto a C18 reverse-phase column and the constituents thereof were eluted with a hydrophobicity gradient between the solvents water-0.1% TFA and acetonitrile-0.1% TFA. The ASICalgin-1 and ASICalgin-2 peptides were eluted pure at 26% and 27% of acetonitrile, respectively.

Peptide Characterization

Amino Acid Analysis

ASICalgin-1 and ASICalgin-2 are two basic isopeptides which have a sequence of 57 amino acids containing 8 cysteines forming 4 disulfide bridges (FIG. 1A, SEQ ID NO: 2 and 3, respectively), and which is preceded by a signal sequence of 21 amino acids (FIG. 1B, cf. SEQ ID NO: 6). They differ from one another only by virtue of an amino acid in position 4 of SEQ ID NO: 1, 2 or 3 (position 25 of SEQ ID NO: 6).

Determination of the Amino Acid Sequence by Cloning

The complete sequence (FIG. 1B) of ASICalgin-1 was determined by cloning the cDNA by PCR, from the messenger RNA (mRNA) present in trace amounts in the crude venom. 25 mg of the venom of the snake *Dendroaspis polylepis* (Sigma) were resuspended in lysis buffer: 500 mM LiCl, 10 mM EDTA, 1% (w/v) LiDS, and 5 mM dithiothreitol in 100 mM of tris-HCl buffer, pH 7.5. The messenger RNA was captured by means of magnetic beads grafted with dT25 oligonucleotides (Dynal, UK). These oligonucleotides were directly used as primers for carrying out the reverse transcription of the mRNA to cDNA with the PrimeScript™ reverse transcriptase (TaKaRa Bio Inc., Japan). The resulting solid-phase cDNA library was used to carry out a degenerate PCR with the sense (TGITTYCARCAYGGIAARGT, SEQ ID NO: 7) and antisense (YTTIARRTTICGRAAIGGCAT, SEQ ID NO: 8) oligonucleotides defined from the partial protein sequence of the toxin determined by direct N-terminal sequencing. In order to exclude any error due to the polymerase, three independent PCRs were carried out, which produced fragments at the hoped for size (89 base pairs), that were subsequently subcloned into the pGEMTeasy vector (Promega) and sequenced. By virtue of these sequences, a specific sense oligonucleotide with an added EcoRI restriction site was synthesized (ACAC(GAATTC)GCTATCATAACACTGGCATG, SEQ ID NO: 9), as was a nonspecific poly-dT30 antisense oligonucleotide, also with an added EcoRI site (ACAC(GAATTC)dT30, SEQ ID NO: 10). These two oligonucleotides made it possible to amplify by PCR the entire 3'-coding and 3'-noncoding end for identification purposes. Three independent PCRs generated a band of approximately 400 base pairs and the subcloning thereof into the pGEMTeasy vector at the EcoRI restriction site made it possible to sequence it while excluding any error generated by the polymerase.

On the basis of the 3'- and 5'-noncoding sequences, a sense oligonucleotide (ACAC(GAATTC)TCCAGAGAAGATCGCAAGATG, SEQ ID NO: 11) and an antisense oligonucleotide (ACAC(GAATTC)ATTTAGCCACTCGTAGAGCTA, SEQ ID NO: 12) framing the coding sequence were synthesized. Four independent PCRs were carried out on the solid-phase cDNA library and the PCR products were again subcloned into the pGEMTeasy vector so as to obtain the complete nucleotide sequence of the ASICalgin-1 toxin precursor.

Peptide Sequencing

The sequence was confirmed up to amino acid Asp40 by direct N-terminal sequencing of the reduced and alkylated peptides on an automatic sequencer (LC491, Applied Biosystems, USA).

Enzymatic Cleavage

In order to confirm the sequences, the peptides were subjected to the following enzymatic treatments: (a) V8 protease with separation of the digested peptides on a C18 reverse phase HPLC column. The cleavage in position D15 and E43 and the separation on HPLC of two peptides of molecular weight 1786.9 Da (peptide 1-15), entirely resequenced, and 3194.5 Da (peptide 16-43), partial sequence, make it possible to confirm the N-terminal sequence. (b) Trypsin digestion with direct analysis by mass spectrometry. The tryptic fragments also confirm the N-terminal sequence and also other parts of the peptide sequence of the ASICalgins. The tryptic peptides detected and sequenced by MS/MS analysis are given in table 1 below.

TABLE 1

| Position | Peptide sequence | Mw (Da) |
|---|---|---|
| 3-8 | CFQHGK (SEQ ID NO: 13) | 775.27 |
| 3-8 | CYQHGK (SEQ ID NO: 14) | 791.27 |
| 3-14 | CFQHGKVVTCHR (SEQ ID NO: 15) | 1527.58 |
| 3-14 | CYQHGKVVTCHR (SEQ ID NO: 16) | ND |
| 9-14 | VVTCHR (SEQ ID NO: 17) | 770.31 |
| 15-28 | DMKFCYHNTGMPFR (SEQ ID NO: 18) | 1803.57 |
| 32-48 | LILQGCSSSCSETENNK (SEQ ID NO: 19) | 1925.63 |
| 49-54 | CCSTDR (SEQ ID NO: 20) | 797.24 |
| 32-54 | LILQGCSSSCSETENNKCCSTDR (SEQ ID NO: 21) | 2705.78 |

Mass Spectrometry (MALDI-TOF)

In all cases, the mass spectrometry analysis was carried out on a 4800 MALDI-TOF-TOF spectrometer (Applied Biosystems, USA).

The native proteins were analyzed in positive ion linear mode with a sinapinic acid matrix (Sigma Aldrich, USA) using an internal calibration with a mixture of proteins of known molecular weight.

The molecular weight measured is 6554.8 Da for ASICalgin-1 and 6538.4 for ASICalgin-2. It is in perfect agreement with the molecular weights calculated via the sequence, 6554.58 Da and 6538.58 Da, respectively, on the GPMAW protein analysis software. These results suggest a free carboxylic acid C-terminal end. The molecular absorbance calculated at 280 nm is $\epsilon$=3040 (for ASICalgin-1) and $\epsilon$=1760 (for ASICalgin-2).

Database Search for Homologues

ASICalgin-1 and ASICalgin-2 do not appear in the databases and do not exhibit any total sequence identity with other already known peptides or toxins.

The BLAST sequence alignment program shows that ASICalgin-1 and ASICalgin-2 nevertheless exhibit 47% to 55% sequence identity (63% to 66% sequence homology) with the peptides CM-1b, CM-3 and CM-2a purified from the venoms of various species of cobra snakes (Naja and Ringhals), and also with an $\alpha$-neurotoxin, OH-26, present in the venom of the king cobra *Ophiophagus hannah*. However, these CM and OH-26 neurotoxins are not described as acting on ASIC channels nor as exhibiting analgesic effects in vivo, but rather as exhibiting cytotoxic effects. It therefore appears that, below 55% sequence identity with ASICalgin-1 or ASICalgin-2, the biological properties exhibited by the peptides of the invention are lost. On the other hand, it is known from the art that isoform and/or orthologous toxins exhibit a preserved activity despite some differences in their protein sequences resulting in a sequence identity of about 70%. It therefore appears that isoform and/or orthologous toxins which exhibit a sequence identity of at least 56% to 70% with ASICalgin-1 or ASICalgin-2 will retain the properties of said peptides of the invention.

Example 2

Analgesic effect of the ASICalgin-1 (π-dpi) and ASICalgin-2 (π-Dp2) Peptides In Vivo after Intrathecal Injection The pain behavior of mice (C57B16J, 7- to 11-week-old males) was evaluated after intrathecal (IT) injection of the peptides between the L5 and L6 vertebrae, according to the protocol of Hylden and Wilcox [1980] [35]. The effects of an IT injection of 10 μl of solution containing 34 μM of ASICalgin-1 (0.34 nmol) or 20 μM of ASICalgin-2 (0.2 nmol) were compared with the effects of an IT injection of 10 μl of solution containing 3.1 mM of morphine (31 nmol) or of 10 μl of saline solution vehicle (145 mM NaCl, 5 mM KCl, 2 mM $CaCl_2$, 10 mM HEPES, pH 7.4, 0.05% bovine serum albumin). In certain series of experiments, naxolone, an inhibitor of opioid receptors (especially of μ type), was injected subcutaneously at 2 mg/kg in 50 μl of 0.9% NaCl, ten minutes before the IT injection of the ASICalgin peptide.

Toxicity

The intrathecal injection of the ASICalgin-1 and ASICalgin-2 peptides induces no modification of behavior of motor problem, balance problem, apathy, paralysis or convulsion type, nor any deaths, in mice.

Acute Chemical Pain and Inflammatory Pain

The subcutaneous injection of formol (15 μl at 2% in a 0.9% NaCl solution) into the arch of the hind paw of a mouse induces pain exhibiting two phases: a phase I of acute chemical pain for 10 minutes and a phase II of inflammatory pain for 15 to 45 minutes (FIG. 2A).

The pain is measured by observing the spontaneous pain behavior of the animal, i.e. by counting the time during which the mouse raises the injected paw, licks it, chews at it or shakes it (integrated voluntary behavior).

The IT injection of ASICalgin-1 significantly reduces the phase I pain by 40% and the phase II pain by 70%. This analgesic effect is similar to that of morphine (FIG. 2B).

The IT injection of ASICalgin-2 produces an effect identical to ASICalgin-1.

The pretreatment with naxolone, an opiate receptor inhibitor, has no effect on the analgesic effect of ASICalgin-1, whether it be on either of the two pain phases I and II (FIG. 2B).

The ASICalgin-1 and ASICalgin-2 peptides are the first analgesic peptides extracted from the venom of *Dendroaspis polylepis.*

Acute Thermal Pain

The thermal pain was studied in mice by measuring the latency of withdrawal of the tail immersed in water at 46° C. (reflex movement, the animal is braced), with a limiting duration of 30 s.

The ASICalgin-1 peptide induces an analgesic effect which is as powerful as that of morphine (7 minutes after the IT injection), but which is more transient at the concentration used (FIG. 2C).

The analgesic effect of ASICalgin-1 is not significantly inhibited by a pretreatment with naxolone (FIG. 2D).

Inflammatory Hyperalgesia

The subcutaneous injection of 2% carrageenan into the arch of the hind paw of the mice leads to the development of a tissue inflammation and of hyperalgesia, measured by the latency of withdrawal of the hind paw immersed in water at 46° C. (integrated voluntary movement, the animal is braced) with a limiting duration of 30 s, two hours after the injection of carrageenan (FIG. 2E, #).

The IT injection of ASICalgin-1 leads to rapid analgesia, comparable to that of morphine and persisting throughout the duration of the experiment (67 minutes, FIG. 2E).

The analgesic effect of ASICalgin-1 is only slightly inhibited by 20% by a pretreatment with naxolone (FIG. 2F).

Motor Activity

The effects of the ASICalgin-1 peptide on motor activity were evaluated by means of the accelerating rotarod test. The mice were placed on an axle rotating at four rotations per minute (rpm) which undergoes a constant acceleration of 5 rpm per minute up to 40 rpm. The latency to fall is measured, with a maximum limit of 300 s.

The IT injection of the ASICalgin-1 peptide does not induce any significant effect (ANOVA test) on the performance levels of the mice with regard to motor activity compared with an injection of vehicle solution.

Example 3

Analgesic effect of the ASICalgin-1 peptide (π-Dp1) in Vivo after Intracerebroventricular Injection The intracerebroventricular (ICV) injection of the ASICalgin-1 peptide was carried out in the third ventricle of the brain of mice (C57B16J, 7- to 11-week-old males) anesthetized with isoflurane (1.5%) using the following stereotaxic coordinates: −2.4 mm under the cortical surface, −0.5 mm in the anterior-posterior axis and +1.6 mm in the mediolateral axis relative to the bregma. The effects of an ICV injection of 5 μl of solution containing 34 μm of ASICalgin-1 (0.34 nmol) were compared with the effects of 5 μl of saline solution vehicle (145 mM NaCl, 5 mM KCl, 2 mM $CaCl_2$, 10 mM HEPES, pH 7.4, 0.05% bovine serum albumin) naxolone, an inhibitor of opioid receptors (especially μ-type), was injected subcutaneously at 2 mg/kg in 50 μl of 0.9% NaCl, ten minutes before the ICV injection of the ASICalgin-1 peptide.

Toxicity

The ICV injection of the ASICalgin-1 peptide induces no modification of behavior of motor problem, balance problem, apathy, paralysis or convulsion type, nor any deaths in the mice, even after 3 days.

Acute Thermal Pain

The thermal pain was studied in mice by measuring the latency of withdrawal of the tail immersed in water at 46° C. (reflex movement, the animal is braced) with a limiting duration of 30 s.

Figure 3:
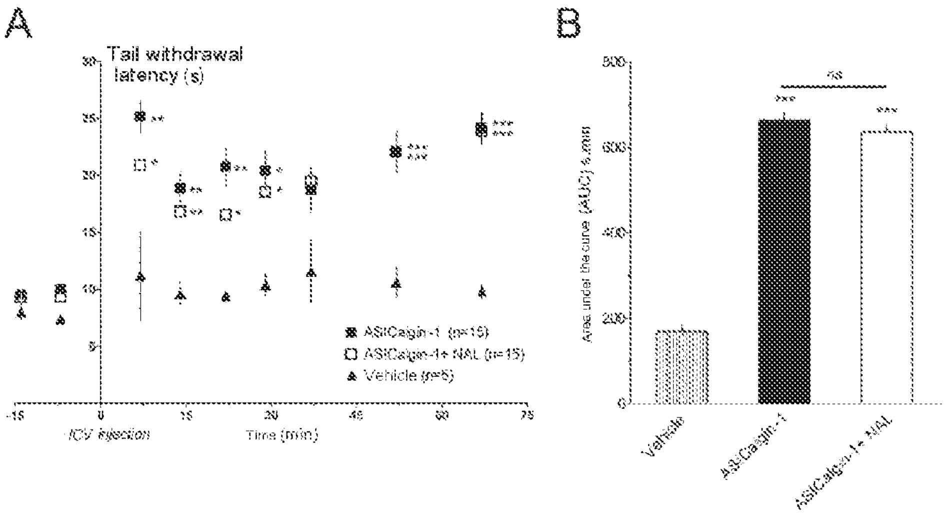
FIG. 3 represents the analgesic effect of the ASICalgin-1 (π-Dp1) peptide in vivo after intracerebroventricular injection in mice in the acute thermal pain test: (A) kinetics of tail withdrawal latency, (B) mean of the areas under the curve (AUC) measured for each animal. The mean values±sem (standard error of the mean) are represented. The number (n) of animals tested is mentioned in the legends. Significance relative to the injection of the vehicle or else according to where indicated on the figure with a line: not significant ns, $p>0.05$; *, $p<0.05$; , $p<0.01$; *, $p<0.001$; by ANOVA followed by a Newman Keuls multiple comparison.

The ICV injection of the ASICalgin-1 peptide induces a powerful analgesic effect which is maintained throughout the duration of the experiment (67 min, FIG. 3), which effect is not modified by a pretreatment with naloxone. The analgesic effect persists for several hours before the value of the tail withdrawal latency returns to its control value.

Example 4

Analgesic effect of the ASICalgin-1 peptide (π-Dp1) in Vivo after Subcutaneous Injection The effect of a subcutaneous (SC) injection of the ASICalgin-1 peptide was tested on carrageenan-induced inflammatory hyperalgesia.

The SC injection of 2% carrageenan into the arch of the hind paw of the mice (C57B16J, 7- to 11-week-old males) leads to the development of a tissue inflammation and of hyperalgesia, measured by the latency of withdrawal of the hind paw immersed in water at 46° C. (integrated voluntary movement, the animal is braced) with a limiting duration of 30 s, two hours after the injection of carrageenan.

Figure 4:
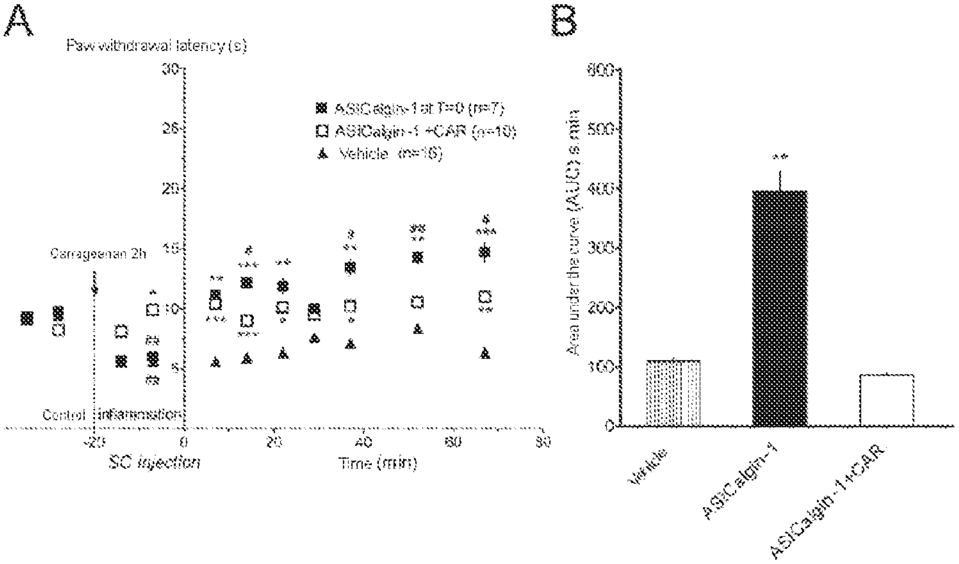
FIG. 4 represents the analgesic effect of the ASICalgin-1 (π-Dp1) peptide in vivo after subcutaneous injection in the inflammatory hyperalgesia test: (A) kinetics of paw withdrawal latency. The ASICalgin-1 peptide is injected subcutaneously into the left rear paw at the same time as the carrageenan (□) then again two hours later (times 0 or T0, □). A similar procedure is carried out, but with injection of the ASICalgin-1 peptide only at T0, i.e. after the appearance of the inflammatory hyperalgesia (■). (B) Mean of the areas under the curve (AUC) estimated for each animal, from the value at T−7 min. The mean values±sem are represented. The number (n) of animals tested is mentioned in the legends. Significance relative to the injection of the vehicle: *, $p<0.05$; , $p<0.01$; *, $p<0.001$; by ANOVA test followed by a Newman Keuls multiple comparison. Significance relative to the control value before the injection of carrageenan: #, $p<0.05$; ##, $p<0.01$; ###, $p<0.001$; by paired T-test.

When the ASICalgin-1 peptide (10 μl of solution containing 34 μM of ASICalgin-1 (0.34 nmol) in 0.9% NaCl, 0.05% bovine serum albumin) is coinjected with the carrageenan, no thermal inflammatory hyperalgesia is observed (FIG. 4, □). Under these conditions, a second SC injection of the ASICalgin-1 peptide two hours later produces no additional significant effect (FIG. 4, □).

If the ASICalgin-1 peptide was not coinjected with the carrageenan, the SC injection of said peptide when the inflammation is already established, two hours after the injection of carrageenan alone, reverses the inflammatory hyperalgesia and furthermore produces significant analgesia compared with the control condition, before the injection of carrageenan (FIG. 4, ■ and #).

Example 5

Activity of the ASICalgin-1 (π-Dp1) and ASICalgin-2 (π-Dp2) Peptides on the ASIC Currents The ASICalgin-1 and ASICalgin-2 peptides inhibit the currents generated by the ASIC channels heterologously expressed in the COS cell line and recorded using the patch-clamp technique in "whole cell" configuration ("applied potential" mode).

The peptides are applied at pH 7.4, 30 seconds before the extracellular pH drop from 7.4 to 6 or 5.5.

The ASICalgin-1 and ASICalgin-2 peptides have the same effect, and inhibit the current generated by the rat homomeric ASIC1a channels with a concentration that produces 50% inhibition ($IC_{50}$) of 49 nM (FIG. 5A), and the current generated by the human homomeric ASIC1a channels with an $IC_{50}$ of 127 nM (FIG. 5B). The current generated by the rat homomeric ASIC1b channels is inhibited with an $IC_{50}$ of 650 nM (FIG. 5C), the rat and human heteromeric ASIC 1a+ASIC2a channels with an $IC_{50}$ of 308 nM (FIG. 5E), and the rat heteromeric ASIC1a+ASIC1b channels with an $IC_{50}$ of 223 nM (FIG. 5D) (the ASIC1b channel was not described in humans).

The ASICalgin-1 and ASICalgin-2 peptides do not inhibit the rat and human homomeric ASIC2a and ASIC3 channels, nor the rat heteromeric ASIC1a+ASIC3 and ASIC1b+ASIC3 channels.

Figure 5:
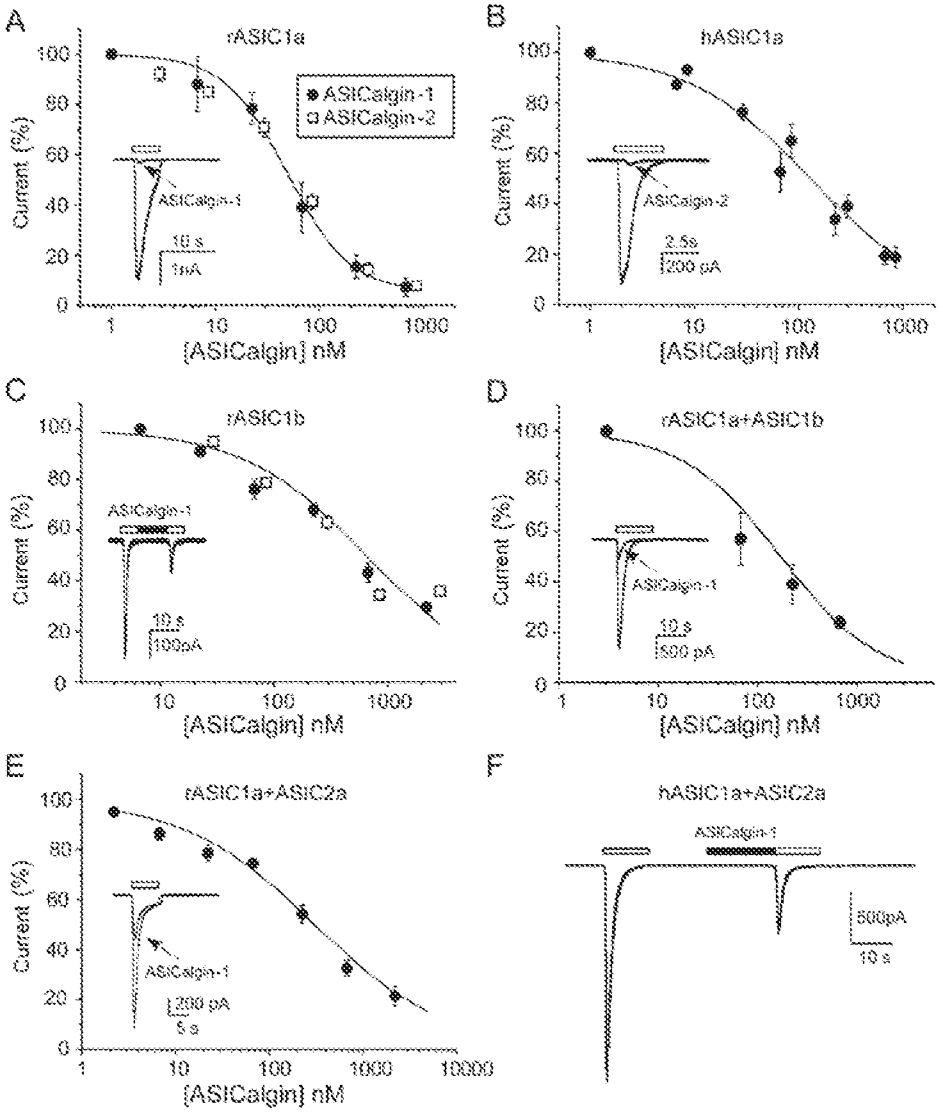
FIG. 5 represents the inhibition, by the ASICalgin-1 (π-Dp1) and ASICalgin-2 (π-Dp2) peptides, of the currents generated by the ASIC channels heterologously expressed in COS cells. Dose-response curve of the inhibition by ASICalgin-1 (π-Dp1) of the rat homomeric ASIC1a current, $IC_{50}$=49 nM (A), of the human homomeric ASIC1a current, $IC_{50}$=127 nM (B), of the rat homomeric ASIC1b current, $IC_{50}$=650 nM (C), of the rat heteromeric ASIC1a+ASIC1b (ratio 1:1) current, $IC_{50}$=223 nM (D), and of the rat heteromeric ASIC 1a+ASICa (2:1 ratio) current, $IC_{50}$=308 nM (E). The mean values±sem are indicated, with n from 4 to 15 experiments. Original plots of currents inhibited by ASICalgin-1 (π-Dp1, 674 nM) and ASICalgin-2 (π-Dp2, 852 nM) are shown in miniature. (F) Original plots of current showing the inhibition of the human heteromeric ASIC1a+ASIC2a (2:1 ratio) current by ASICalgin-1 (π-Dp1, 674 nM). Resting potential: −60 mV, white bars: drop in pH from 7.4 to 5.5, black bars: application of the peptide.

The effects of the ASICalgin-1 and ASICalgin-2 peptides are reversible once the application of the peptides is stopped (FIG. 5).

The ASICalgin-1 and ASICalgin-2 peptides are the only peptides described today that are capable of inhibiting the homomeric ASIC1b channels and the heteromeric ASIC1a+ASIC1b and ASIC1a+ASIC2a channels.

On the other hand, the ASICalgin-1 peptide (2 μM) does not inhibit the current produced by rat TRPV1 channels activated with capsaicin (1 μM), which are channels also involved in the transduction of pain by sensory nerve endings.

Without being limited to this explanation, the analgesic effects of the ASICalgin-1 and ASICalgin-2 peptides appear to involve the inhibition of the homomeric ASIC1a channels and heteromeric ASIC1a+ASIC2a channels in central nervous system neurons (IT and ICV injections), and the inhibition of the homomeric ASIC1a and ASIC1b channels and heteromeric ASIC1a+ASIC1b channels in sensory neurons (subcutaneous injection, IT injection with the proviso that homomeric ASIC1a and ASIC1b and heteromeric ASIC1a+ASIC1b are present in the central endings of the sensory neurons at the level of the dorsal horn of the spinal cord).

Example 6

Figure 6:
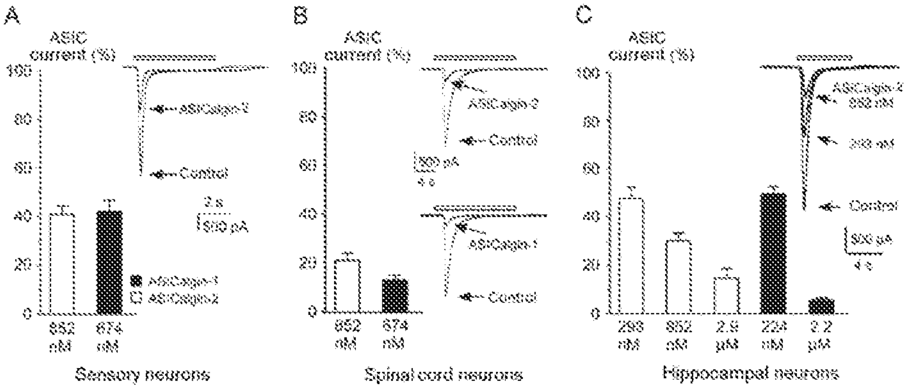
FIG. 6 represents the inhibition, by the ASICalgin-1 (π-Dp1) and ASICalgin-2 (π-Dp2) peptides, of the native ASIC currents of murine sensory and central neurons in culture. (A) Mean inhibition of the ASIC current of sensory neurons of rat (n=34) by ASICalgin-2 (π-Dp2, 852 nM, □) and ASICalgin-1 (π-Dp1, 674 nM, ■). On the right, examples of original currents recorded at the resting potential of −50 mV and activated with a drop in pH of from 7.4 to 6 (white bar). In the sensory neurons, the total ASIC current results from a mixture of homomeric ASIC1a current, of current of ASIC1b type and of current of ASIC3 type. (B) Mean inhibition of the ASIC current of dorsal cord neurons of mice (n=18) by ASICalgin-2 (π-Dp2, 852 nM, □) and ASICalgin-1 (π-Dp1, 674 nM, ■). On the right, example of original currents recorded at the resting potential of −50 mV and activated with a drop in pH of from 7.4 to 6 (white bar). (C) Mean inhibition of the ASIC current of hippocampal neurons of mice (n=26) by ASICalgin-2 (π-Dp2, 293 nM, 852 nM and 2.9 μM, □) and ASICalgin-1 (π-Dp1, 224 nM and 2.2 μM, ■). On the right, example of original currents recorded at the resting potential of −50 mV and activated with a drop in pH of from 7.4 to 5.5 (white bar). In the central neurons (mouse cord and hippocampus), the total ASIC current results from a mixture of homomeric ASIC1a current and of heteromeric ASIC1a+ASIC2a current. The mean values±sem are indicated.

Activity of the ASICalgin-1 (π-Dp1) and ASICalgin-2 (π-Dp2) Peptides on the Native ASIC Currents of Central Neurons and of Sensory Neurons The ASICalgin-1 and ASICalgin-2 peptides reversibly inhibit the ASIC currents recorded using the patch-clamp technique in "whole cell" configuration ("applied potential" mode) in neurons in primary culture isolated from adult rat spinal ganglia (FIG. 6A), from mouse embryo dorsal spinal cord (FIG. 6B), and from newborn mouse (2 days) hippocampus (FIG. 6C).

The partial inhibitory effect of the ASICalgin-1 and ASICalgin-2 peptides on the total ASIC current of sensory neurons is explained by the large proportion of current of ASIC3 type (not inhibited by the ASICalgin-1 and ASICalgin-2 peptides) in sensory neurons, whereas the central (hippocampus and spinal cord) ASIC currents are composed of a mixture of homomeric ASIC 1a and heteromeric ASIC1a+ASIC2a currents (both inhibited by the ASICalgin-1 and ASICalgin-2 peptides).

Example 7

Activity of the ASICalgin-1 (π-Dp1) and ASICalgin-2 (π-Dp2) Peptides on Neurons

The ASICalgin-1 and ASICalgin-2 peptides applied to spinal neurons in culture do not induce any modification of the basal current level, nor any variations in resting potential (FIG. 7A) recorded using the patch-clamp technique in "whole cell" configuration.

Figure 7:
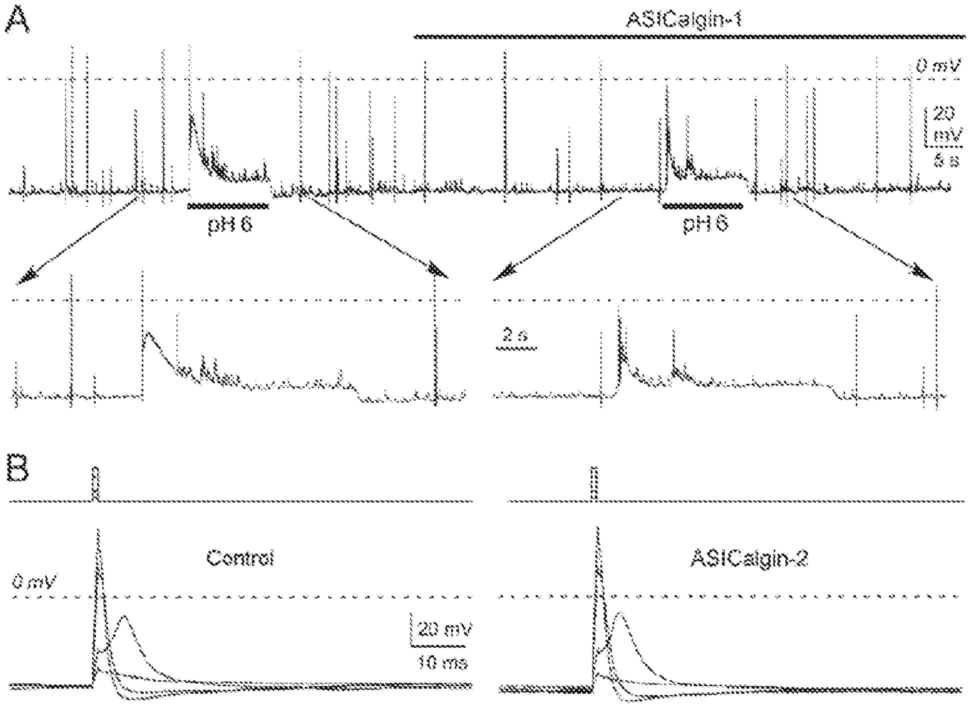
FIG. 7 represents the effect of the ASICalgin-1 (π-Dp1) and ASICalgin-2 (π-Dp2) peptides on the membrane potential of mouse dorsal spinal cord neurons. (A) Membrane potential of a neuron where the spontaneous action potentials reflect synaptic activity (dashed line: 0 mV). The activation of the ASIC current by a drop in pH of from 7.4 to 6 induces a depolarization of which the peak triggers an action potential (enlargement). The application of the ASICalgin-1 peptide (π-Dp1, 674 nM) does not modify the resting potential of the neuron nor the spontaneous activity. On the other hand, the depolarization induced by the acid pH drop is reduced and no longer induces an action potential. (B) Action potential evoked by an electric stimulation (square-wave currents represented above). Four responses are superimposed (left-hand panel): two subliminal depolarizations and two others triggering an action potential (dashed line: 0 mV). The application of ASICalgin-2 (π-Dp2, 852 nM, right-hand panel) does not modify the excitability of the neuron.

The application of the ASICalgin-1 and ASICalgin-2 peptides does not modify the spontaneous synaptic electrical activity of spinal neurons in culture, nor the shape or the threshold of action potentials evoked by an electrical stimulation ("applied current" mode of the patch clamp) (FIG. 7B).

The results show that the ASICalgin-1 and ASICalgin-2 peptides have no effect on the intrinsic excitability properties of neurons, on synaptic function or on potential-dependent currents involved in the generation ($Na^+$ channels) or repolarization ($K^+$ channels) of action potentials.

On the other hand, the specific inhibition of ASIC channels by the ASICalgin-1 and ASICalgin-2 peptides reduces the excitability of neurons in response to an acidic pH drop (from 7.4 to 6.0), the depolarization produced by the ASIC current then not being sufficient to trigger an action potential (FIG. 7A).

REFERENCE LIST

1. Bertin and Vergne-Salle, "Traitements médicamenteux de l'inflammation et des douleurs inflammatoires" ["Drug treatments for inflammation and inflammatory pain"] UPSA Pain Institute—A Editorial Paris, p. 113-132, 2007
2. Gutstein and Akil, "Opioid analgesics", in "The Pharmacological Basis of Therapeutics" Brunton et al., Eds. McGraw-Hill, 2006.
3. Bannister & Dickenson, Curr. Opin. Support Palliat. Care, 4: 1-5, 2010
4. Yennurajalingam et al., Support Cancer Ther., 1: 97-110, 2004
5. Mizoguchi et al., Int. Rev. Neurobiol., 85: 249-260, 2009
6. Waldmann and Lazdunski, Curr. Opin. Neurobiol., 3: 418-424, 1998
7. Wemmie et al., Trends Neurosci., 29: 578-586, 2006
8. Lingueglia et al., J. Biol. Chem., 282: 17325-17329, 2007
9. Jasti et al., Nature, 449: 316-323, 2007
10. Lingueglia et al., J. Biol. Chem., 272: 29778-29783, 1997
11. Benson et al., Proc. Natl. Acad. Sci. U.S.A., 95: 10240-10245, 2002
12. Hesselager et al., J. Biol. Chem., 279: 11006-11015, 2004
13. Waldmann et al., Nature, 386: 173-177, 1997a
14. Noel et al., "Current perspectives on acid-sensing ion channels: new advances and therapeutic implications" Expert Rev. Clin. Pharmacol. "Clinical Pharmacology of Ion Channels", 3: 331-346, 2010
15. Waldmann et al., J. Biol. Chem., 272: 20975-20978, 1997b
16. Bassler et al., J. Biol. Chem., 276: 33782-33787, 2001
17. Chen et al., Proc. Natl. Acad. Sci. U.S.A., 95: 10240-10245, 1998
18. Reeh and Steen, Prog. Brain Res., 113: 143-151, 1996
19. Steen et al., Neurosci. Lett., 199: 29-32, 1995a
20. Issberner et al., Neurosci. Lett., 208: 191-194, 1996
21. Ugawa et al., J. Clin. Invest., 10: 1185-1191, 2002
22. Jones et al., J. Neurosci., 24: 10974-10979, 2004
23. Voilley et al., J. Neurosci., 21: 8026-8033, 2001
24. Dubé et al., Pain, 117: 88-96, 2005
25. Escoubas et al., J. Biol. Chem., 275: 25116-25121, 2000
26. Diochot et al., EMBO J., 23: 1516-1525, 2004
27. Deval et al., EMBO J., 27: 3047-3055, 2008
28. Mazzuca et al., Nature Neuroscience, 10: 943-945, 2007
29. Abott et al., Pharmacol. Biochem. Behav., 17(6): 1213-1219, 1982
30. Cridland and Henry, Brain Res., 584(1-2): 163-168, 1992
31. Woolfe and Macdonald, J. Pharmacol. Exp. Ther., 80: 300-307, 1944
32. Ankier, Eur. J. Pharmacol., 27(1): 1-4, 1974
33. Kim et al., Pain, 55: 85-92, 1993
34. U.S. Pat. No. 5,877,026
35. Hylden and Wilcox, Eur. J. Pharmacol., 67: 313-316, 1980
36. Deval et al., J. Neurosci., 31(16): 6059-6066, 2011

The invention claimed is:

1. A method of treating pain in a patient using an isolated peptide having an analgesic activity, said isolated peptide comprising an amino acid sequence LKCX$^4$QHGK VVTCHRDMKFCYHNTGMPFRNLKLILQGCSSSCS ETENNKCCSTDRCNK (SEQ ID NO: 1), wherein X$^4$ represents any amino acid, or a sequence exhibiting an identity of at least 98% with the sequence SEQ ID NO: 1 and retaining the analgesic activity of said peptide comprising the sequence SEQ ID NO: 1; the method comprising:

administering said isolated peptide to the patient.

2. The method of claim 1, wherein said isolated peptide is a blocker of at least one ASIC channel.

3. The method of claim 2, wherein said isolated peptide is a blocker of at least one ASIC channel containing at least one subunit chosen from the group consisting of the ASIC1a and ASIC1b subunits.

4. The method of claim 3, wherein said isolated peptide is a blocker of the homomeric ASIC1a channel, homomeric ASIC1b channel, heteromeric ASIC1a+ASIC1b channel and/or heteromeric ASIC1a+ASIC2a channel.

5. The method of claim 4, wherein X$^4$ represents Y or F in the sequence SEQ ID NO: 1.

6. The method of claim 1, wherein said isolated peptide is administered to the patient by an administration route chosen from orally, intramuscularly, intravenously, subcutaneously, topically, via the pulmonary route, intranasally, buccally, rectally, sublingually, intradermally, intraperitoneally and intrathecally.

7. The method of claim 1, wherein X$^4$ represents Y or F in the sequence SEQ ID NO: 1.

8. A method of treating pain in a patient, the method comprising:

administering a pharmaceutical composition having an analgesic activity to a patient, said pharmaceutical composition comprising one or more isolated peptides having an amino acid sequence LKCX$^4$QHGK VVTCHRDMKFCYHNTGMPFRNLKLILQGCSSS CSETENNKCCSTDRCNK (SEQ ID NO: 1), wherein X$^4$ represents any amino acid, or a sequence exhibiting an identity of at least 98% with the sequence SEQ ID NO: 1 and retaining the analgesic activity of said peptide comprising the sequence SEQ ID NO: 1.

9. The method of claim 8, wherein the analgesic is intended for the prevention or treatment of pain or of a pathological condition involving the activation of ASIC channels.

10. The method of claim 9, wherein the pain and the pathological condition involving the activation of ASIC channels are chosen from the group comprising inflammatory, neuropathic, cancer-related, post-operative, musculoskeletal and visceral pain, inflammations, cancers, fibromyalgia and irritable bowel syndrome.

11. The method of claim 8, wherein said pharmaceutical composition is intended for the prevention or treatment of a central neurological disease chosen from the group comprising depression, anxiety, strokes, epilepsy, central inflammations and neurodegenerative diseases.

12. The method of claim 8, wherein said pharmaceutical composition is administered centrally, subcutaneously, transcutaneously, systemically, orally or by the respiratory route.

13. The method of claim 8, wherein the pharmaceutical composition is administered intrathecally and an effective analgesic amount of the isolated peptide is in the range of 5 ng/kg to 500 μg/kg of a bodyweight of the patient.

14. The method of claim 13, wherein the effective analgesic amount is in the range of 50 ng/kg to 50 μg/kg of the bodyweight of the patient.

15. The method of claim 13, wherein the effective analgesic amount is in the range of 500 ng/kg to 5 μg/kg of the bodyweight of the patient.

16. The method of claim 8, wherein the pharmaceutical composition comprises one or more acceptable vehicles.

17. The method of claim 16, wherein the one or more acceptable vehicles are chosen from calcium carbonate, starch, talc, lactose, magnesium stearate and acacia gum.

18. The method of claim 8, wherein the pharmaceutical composition is in the form chosen from a solution, suspension, paste, gel capsule, tablet, capsule, powder, granule, lyophilisate, controlled-release system, microparticle, microsphere, nanosphere and liposome.

19. A method of using one or more isolated peptides as a diagnostic tool to identify a compound that mimics an analgesic activity of said one or more isolated peptides, said one or more peptides comprising an amino acid sequence LKCX$^4$QHGKVVTCHRDMKFCYHNTGMPFRNLKLIL QGCSSSCSETENNKCCSTDRCNK (SEQ ID NO: 1), wherein X$^4$ represents any amino acid, or a sequence exhibiting an identity of at least 98% with the sequence SEQ ID NO: 1 and retaining the analgesic activity of said peptide comprising the sequence SEQ ID NO: 1, said method comprising:

a) determining the analgesic activity of said one or more peptides;

b) determining the analgesic activity of a candidate compound;

c) comparing the analgesic activities obtained in steps a. and b.; and d) selecting the candidate compound which has an analgesic activity equivalent to or greater than that of said one or more peptides.

20. A method of using a peptide as a diagnostic tool to identify a compound that mimics an analgesic activity of said peptide, said peptide comprising an amino acid sequence LKCX$^4$QHGKVVTCHRDMKFCYHNTGMPFRNLKLIL QGCSSSCSETENNKCCSTDRCNK (SEQ ID NO: 1), wherein X$^4$ represents any amino acid, or a sequence exhibiting an identity of at least 98% with the sequence SEQ ID NO: 1 and retaining the analgesic activity of said peptide comprising the sequence SEQ ID NO: 1, said method comprising:

a) determining the analgesic activity of said peptide;

b) determining the analgesic activity of a candidate compound;

c) comparing the analgesic activities obtained in steps a. and b.; and d) selecting the candidate compound which has an analgesic activity equivalent to or greater than that of said peptide.

* * * * *

SEQUENCE LISTING

```
<160> NUMBER OF SEQ ID NOS: 22

<210> SEQ ID NO 1
<211> LENGTH: 57
<212> TYPE: PRT
<213> ORGANISM: Dendroaspis polylepis
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Leu Lys Cys Xaa Gln His Gly Lys Val Val Thr Cys His Arg Asp Met
1               5                   10                  15

Lys Phe Cys Tyr His Asn Thr Gly Met Pro Phe Arg Asn Leu Lys Leu
            20                  25                  30

Ile Leu Gln Gly Cys Ser Ser Ser Cys Ser Glu Thr Glu Asn Asn Lys
        35                  40                  45

Cys Cys Ser Thr Asp Arg Cys Asn Lys
    50                  55


<210> SEQ ID NO 2
<211> LENGTH: 57
<212> TYPE: PRT
<213> ORGANISM: Dendroaspis polylepis

<400> SEQUENCE: 2

Leu Lys Cys Tyr Gln His Gly Lys Val Val Thr Cys His Arg Asp Met
1               5                   10                  15

Lys Phe Cys Tyr His Asn Thr Gly Met Pro Phe Arg Asn Leu Lys Leu
            20                  25                  30

Ile Leu Gln Gly Cys Ser Ser Ser Cys Ser Glu Thr Glu Asn Asn Lys
        35                  40                  45
```

```
Cys Cys Ser Thr Asp Arg Cys Asn Lys
    50                  55


<210> SEQ ID NO 3
<211> LENGTH: 57
<212> TYPE: PRT
<213> ORGANISM: Dendroaspis polylepis

<400> SEQUENCE: 3

Leu Lys Cys Phe Gln His Gly Lys Val Val Thr Cys His Arg Asp Met
1               5                   10                  15

Lys Phe Cys Tyr His Asn Thr Gly Met Pro Phe Arg Asn Leu Lys Leu
            20                  25                  30

Ile Leu Gln Gly Cys Ser Ser Ser Cys Ser Glu Thr Glu Asn Asn Lys
        35                  40                  45

Cys Cys Ser Thr Asp Arg Cys Asn Lys
    50                  55


<210> SEQ ID NO 4
<211> LENGTH: 237
<212> TYPE: DNA
<213> ORGANISM: Dendroaspis polylepis
<220> FEATURE:
<221> NAME/KEY: misc_feature
<222> LOCATION: (74)..(74)
<223> OTHER INFORMATION: n corresponds to a or t
<220> FEATURE:
<221> NAME/KEY: misc_feature
<222> LOCATION: (75)..(75)
<223> OTHER INFORMATION: n corresponds to c or t

<400> SEQUENCE: 4

atgaaaactc tgctgctgac cttgctggtg gtgacaatcg tgtgcctaga cttaggatac      60

tccctgaaat gttnncaaca tggtaaagtt gtgacttgtc atcgagatat gaagttttgc     120

tatcataaca ctggcatgcc ttttcgaaat ctcaagctca tcctacaggg atgttcttct     180

tcgtgcagtg aaacagaaaa caataagtgt tgctcaacag acagatgcaa caaatag        237


<210> SEQ ID NO 5
<211> LENGTH: 446
<212> TYPE: DNA
<213> ORGANISM: Dendroaspis polylepis
<220> FEATURE:
<221> NAME/KEY: CDS
<222> LOCATION: (1)..(237)
<220> FEATURE:
<221> NAME/KEY: sig_peptide
<222> LOCATION: (1)..(63)
<220> FEATURE:
<221> NAME/KEY: polyA_site
<222> LOCATION: (446)..(446)

<400> SEQUENCE: 5

atg aaa act ctg ctg ctg acc ttg ctg gtg gtg aca atc gtg tgc cta       48
Met Lys Thr Leu Leu Leu Thr Leu Leu Val Val Thr Ile Val Cys Leu
1               5                   10                  15

gac tta gga tac tcc ctg aaa tgt tac caa cat ggt aaa gtt gtg act       96
Asp Leu Gly Tyr Ser Leu Lys Cys Tyr Gln His Gly Lys Val Val Thr
            20                  25                  30

tgt cat cga gat atg aag ttt tgc tat cat aac act ggc atg cct ttt      144
Cys His Arg Asp Met Lys Phe Cys Tyr His Asn Thr Gly Met Pro Phe
        35                  40                  45

cga aat ctc aag ctc atc cta cag gga tgt tct tct tcg tgc agt gaa      192
Arg Asn Leu Lys Leu Ile Leu Gln Gly Cys Ser Ser Ser Cys Ser Glu
    50                  55                  60
```

-continued

```
aca gaa aac aat aag tgt tgc tca aca gac aga tgc aac aaa tag          237
Thr Glu Asn Asn Lys Cys Cys Ser Thr Asp Arg Cys Asn Lys
65                  70                  75

ctctacgagt ggctaaattc attgagtttt gctctcatcc attgtggacc atccttgaaa    297

atttatgctt gtggccttta ccaccagatg gtccatcatc cccctctccc ctgctttctt    357

tgatacctca tcatctttcc cttttctctt gttctgtaat ttccttctgc tagttctgta    417

gtttgagaat caaataaaac tcagcattc                                      446


<210> SEQ ID NO 6
<211> LENGTH: 78
<212> TYPE: PRT
<213> ORGANISM: Dendroaspis polylepis

<400> SEQUENCE: 6

Met Lys Thr Leu Leu Leu Thr Leu Leu Val Val Thr Ile Val Cys Leu
1               5                   10                  15

Asp Leu Gly Tyr Ser Leu Lys Cys Tyr Gln His Gly Lys Val Val Thr
            20                  25                  30

Cys His Arg Asp Met Lys Phe Cys Tyr His Asn Thr Gly Met Pro Phe
        35                  40                  45

Arg Asn Leu Lys Leu Ile Leu Gln Gly Cys Ser Ser Ser Cys Ser Glu
    50                  55                  60

Thr Glu Asn Asn Lys Cys Cys Ser Thr Asp Arg Cys Asn Lys
65                  70                  75


<210> SEQ ID NO 7
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n corresponds to the inosine base capable of
      hybridizing with a, t, g or c
<220> FEATURE:
<221> NAME/KEY: misc_feature
<222> LOCATION: (6)..(6)
<223> OTHER INFORMATION: y can be t or c
<220> FEATURE:
<221> NAME/KEY: misc_feature
<222> LOCATION: (9)..(9)
<223> OTHER INFORMATION: r can be g or a
<220> FEATURE:
<221> NAME/KEY: misc_feature
<222> LOCATION: (12)..(12)
<223> OTHER INFORMATION: y can be t or c
<220> FEATURE:
<221> NAME/KEY: misc_feature
<222> LOCATION: (15)..(15)
<223> OTHER INFORMATION: n corresponds to the inosine base capable of
      hybridizing with a, t, g or c
<220> FEATURE:
<221> NAME/KEY: misc_feature
<222> LOCATION: (18)..(18)
<223> OTHER INFORMATION: r can be g or a

<400> SEQUENCE: 7

tgnttycarc ayggnaargt                                                 20


<210> SEQ ID NO 8
<211> LENGTH: 21
<212> TYPE: DNA
<213> ORGANISM: Artificial Sequence
```

```
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: y can be t or c
<220> FEATURE:
<221> NAME/KEY: misc_feature
<222> LOCATION: (4)..(4)
<223> OTHER INFORMATION: n corresponds to the inosine base capable of
      hybridizing with a, t, g or c
<220> FEATURE:
<221> NAME/KEY: misc_feature
<222> LOCATION: (6)..(7)
<223> OTHER INFORMATION: r can be g or a
<220> FEATURE:
<221> NAME/KEY: misc_feature
<222> LOCATION: (10)..(10)
<223> OTHER INFORMATION: n corresponds to the inosine base capable of
      hybridizing with a, t, g or c
<220> FEATURE:
<221> NAME/KEY: misc_feature
<222> LOCATION: (13)..(13)
<223> OTHER INFORMATION: r can be g or a
<220> FEATURE:
<221> NAME/KEY: misc_feature
<222> LOCATION: (16)..(16)
<223> OTHER INFORMATION: n corresponds to the inosine base capable of
      hybridizing with a, t, g or c

<400> SEQUENCE: 8

yttnarrttn cgraanggca t                                               21


<210> SEQ ID NO 9
<211> LENGTH: 30
<212> TYPE: DNA
<213> ORGANISM: Artificial Sequence
<220> FEATURE:
<223> OTHER INFORMATION: Oligonucleotide

<400> SEQUENCE: 9

acacgaattc gctatcataa cactggcatg                                      30


<210> SEQ ID NO 10
<211> LENGTH: 40
<212> TYPE: DNA
<213> ORGANISM: Artificial Sequence
<220> FEATURE:
<223> OTHER INFORMATION: Oligonucleotide

<400> SEQUENCE: 10

acacgaattc tttttttttt tttttttttt tttttttttt                           40


<210> SEQ ID NO 11
<211> LENGTH: 31
<212> TYPE: DNA
<213> ORGANISM: Artificial Sequence
<220> FEATURE:
<223> OTHER INFORMATION: Oligonucleotide

<400> SEQUENCE: 11

acacgaattc tccagagaag atcgcaagat g                                    31


<210> SEQ ID NO 12
<211> LENGTH: 31
<212> TYPE: DNA
<213> ORGANISM: Artificial Sequence
<220> FEATURE:
<223> OTHER INFORMATION: Oligonucleotide

<400> SEQUENCE: 12
```

-continued

```
acacgaattc atttagccac tcgtagagct a                                31


<210> SEQ ID NO 13
<211> LENGTH: 6
<212> TYPE: PRT
<213> ORGANISM: Dendroaspis polylepis

<400> SEQUENCE: 13

Cys Phe Gln His Gly Lys
1               5


<210> SEQ ID NO 14
<211> LENGTH: 6
<212> TYPE: PRT
<213> ORGANISM: Dendroaspis polylepis

<400> SEQUENCE: 14

Cys Tyr Gln His Gly Lys
1               5


<210> SEQ ID NO 15
<211> LENGTH: 12
<212> TYPE: PRT
<213> ORGANISM: Dendroaspis polylepis

<400> SEQUENCE: 15

Cys Phe Gln His Gly Lys Val Val Thr Cys His Arg
1               5                   10


<210> SEQ ID NO 16
<211> LENGTH: 12
<212> TYPE: PRT
<213> ORGANISM: Dendroaspis polylepis

<400> SEQUENCE: 16

Cys Tyr Gln His Gly Lys Val Val Thr Cys His Arg
1               5                   10


<210> SEQ ID NO 17
<211> LENGTH: 6
<212> TYPE: PRT
<213> ORGANISM: Dendroaspis polylepis

<400> SEQUENCE: 17

Val Val Thr Cys His Arg
1               5


<210> SEQ ID NO 18
<211> LENGTH: 14
<212> TYPE: PRT
<213> ORGANISM: Dendroaspis polylepis

<400> SEQUENCE: 18

Asp Met Lys Phe Cys Tyr His Asn Thr Gly Met Pro Phe Arg
1               5                   10


<210> SEQ ID NO 19
<211> LENGTH: 17
<212> TYPE: PRT
<213> ORGANISM: Dendroaspis polylepis

<400> SEQUENCE: 19

Leu Ile Leu Gln Gly Cys Ser Ser Ser Cys Ser Glu Thr Glu Asn Asn
1               5                   10                  15
```

-continued

```
Lys


<210> SEQ ID NO 20
<211> LENGTH: 6
<212> TYPE: PRT
<213> ORGANISM: Dendroaspis polylepis

<400> SEQUENCE: 20

Cys Cys Ser Thr Asp Arg
1               5


<210> SEQ ID NO 21
<211> LENGTH: 23
<212> TYPE: PRT
<213> ORGANISM: Dendroaspis polylepis

<400> SEQUENCE: 21

Leu Ile Leu Gln Gly Cys Ser Ser Ser Cys Ser Glu Thr Glu Asn Asn
1               5                   10                  15

Lys Cys Cys Ser Thr Asp Arg
            20


<210> SEQ ID NO 22
<211> LENGTH: 174
<212> TYPE: DNA
<213> ORGANISM: Dendroaspis polylepis
<220> FEATURE:
<221> NAME/KEY: misc_feature
<222> LOCATION: (11)..(11)
<223> OTHER INFORMATION: n corresponds to a or t
<220> FEATURE:
<221> NAME/KEY: misc_feature
<222> LOCATION: (12)..(12)
<223> OTHER INFORMATION: n corresponds to c or t

<400> SEQUENCE: 22

ctgaaatgtt nncaacatgg taaagttgtg acttgtcatc gagatatgaa gttttgctat      60

cataacactg gcatgccttt tcgaaatctc aagctcatcc tacagggatg ttcttcttcg     120

tgcagtgaaa cagaaaacaa taagtgttgc tcaacagaca gatgcaacaa atag           174
```